United States Patent [19]

Marshall

[11] Patent Number: 5,313,167
[45] Date of Patent: May 17, 1994

[54] MOISTURE MEASUREMENT APPARATUS, SYSTEM AND METHOD UTILIZING MICROWAVE OR HIGH FREQUENCY ENERGY

[76] Inventor: Noel H. C. Marshall, Star Rte. 46, Woodside, Calif. 94062

[21] Appl. No.: 771,450

[22] Filed: Oct. 4, 1991

[51] Int. Cl.$^5$ ............................................... F26B 3/34
[52] U.S. Cl. ..................................... 324/632; 324/642; 324/644; 324/643; 73/159; 493/7; 493/37
[58] Field of Search ............... 324/639, 640, 641, 637, 324/632, 687, 642; 493/7, 37; 73/159

[56] References Cited

U.S. PATENT DOCUMENTS

| | | | |
|---|---|---|---|
| 2,692,972 | 10/1954 | Egerton et al. | 324/687 |
| 3,460,031 | 8/1969 | Evans et al. | 324/640 |
| 3,981,082 | 9/1976 | Massey | 324/632 X |
| 4,842,477 | 6/1989 | Stowell | 324/632 |
| 5,059,914 | 10/1991 | Lacombe | 324/632 |

Primary Examiner—Kenneth A. Wieder
Assistant Examiner—Jose M. Solis
Attorney, Agent, or Firm—Flehr, Hohbach, Test, Albritton & Herbert

[57] ABSTRACT

Apparatus for measuring a characteristic of a body of material having first and second substantially parallel coaxial lines with distal extremities in relatively close proximity to each other and adapted to be disposed in close proximity to the body of material. A transmitter is coupled to the first coaxial line for introducing electrical energy in the high frequency to a microwave range into the first coaxial line to cause an electromagnetic field to be established at the distal extremity of the first coaxial line and to extend into the body of material. A receiver is coupled to the second coaxial line for detecting any of the electromagnetic field coupled into it from the first coaxial line. A measurement device is coupled to the receiver means for ascertaining when any change occurs in the coupling of the electromagnetic field from the first coaxial line to the second coaxial line to determine said characteristic of the body of material.

15 Claims, 3 Drawing Sheets

MOISTURE MEASUREMENT APPARATUS, SYSTEM AND METHOD UTILIZING MICROWAVE OR HIGH FREQUENCY ENERGY

This invention relates to a moisture measurement apparatus, system and method utilizing microwave or high frequency energy and more particularly to such a moisture measurement apparatus to and apparatus, system and method for ascertaining the glue applied to corrugated cardboard.

Moisture measurements have heretofore been made in materials by utilizing capacitance type measurements or infrared sensing devices or large area microwave reflection and absorption devices. In the manufacture of corrugated cardboard, it has been found that it is difficult during manufacture of the same to ascertain whether the proper amount of glue has been applied between the internal corrugated sheet and the outer sheets of paper generally called liners. The integrity of these glue joints is critical to the quality of the end product corrugated cardboard in terms of strength and flatness. There is therefore a need for an apparatus, system and method for resolving these difficulties.

In general, it is an object of the present invention to provide apparatus, system and method which utilizes microwave or high frequency energy in non-destructive testing to detect a physical characteristic such as moisture in a body of material.

Another object of the present invention is to provide an apparatus, system and method of the above character in which a highly localized electromagnetic field is utilized.

Another object of the present invention is to provide an apparatus, system and method of the above character in which the disturbances of the electric field are measured to ascertain the physical characteristic.

Another object of the invention is to provide an apparatus, system and method which can be utilized when relative movement is occurring between the sensor and the body of material.

Another object of the invention is to provide an apparatus, system and method of the above character which can be utilized for ascertaining the presence or absence of glue at the joint between a corrugated sheet and a liner by measuring the moisture content of the glue.

Another object of the invention is to provide an apparatus, system and method of the above character in which fine spacial resolution can be obtained.

Additional objects and features of the invention will appear from the following description in which the preferred embodiments are set forth in detail in conjunction with the accompanying drawings.

In general, the apparatus for measuring a physical characteristic of a body of material consists of first and second substantially parallel coaxial lines having distal extremities adapted to be disposed in close proximity to each other and to the body of material. Transmitter means is coupled to the first coaxial line for introducing electrical energy in the high frequency or microwave range into the first coaxial line to cause an electromagnetic field to be established at the distal extremity of the first coaxial line and in the body of material. Receiving means is coupled to the second coaxial line to detect any of the electromagnetic field produced by the first coaxial line which is coupled into the distal extremity of the second coaxial line. Measurement means is coupled to the receiving means for ascertaining the enhancement of the coupling of the electromagnetic field between the distal extremities caused by the presence of moisture in the body of material to thereby ascertain the moisture content in the body of material.

Figure 1:
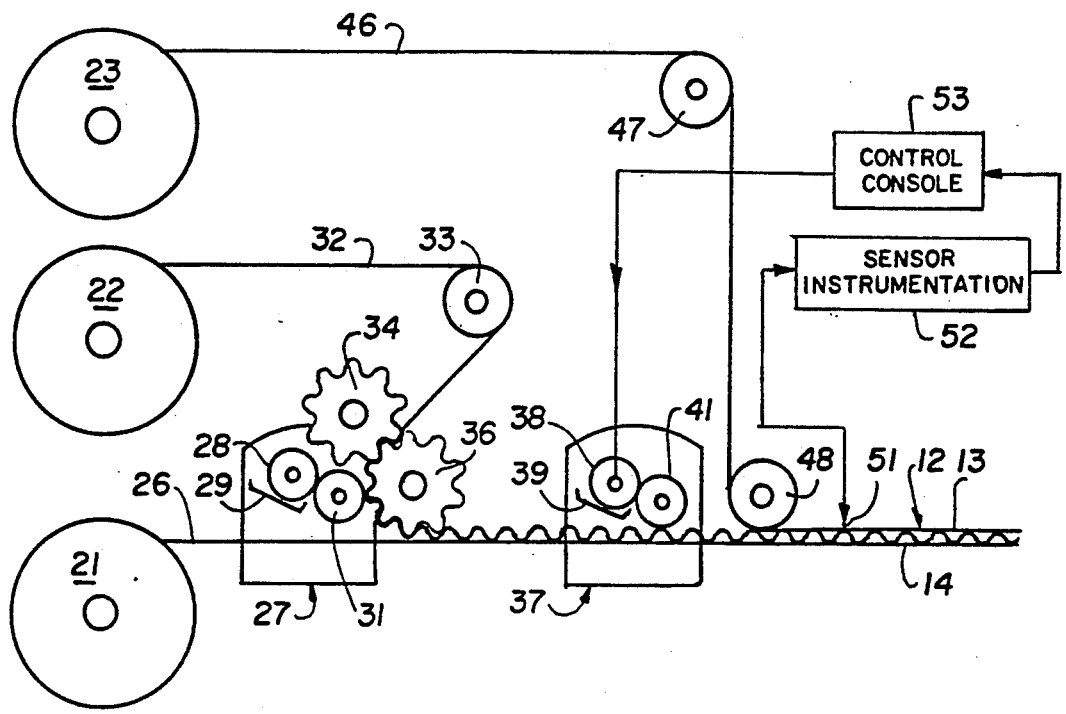
FIG. 1 is a schematic illustration of apparatus and system utilizing microwave or high frequency energy incorporating the present invention for ascertaining the presence or absence of glue in the joints between corrugations and a liner of corrugated cardboard.
Figure 8:
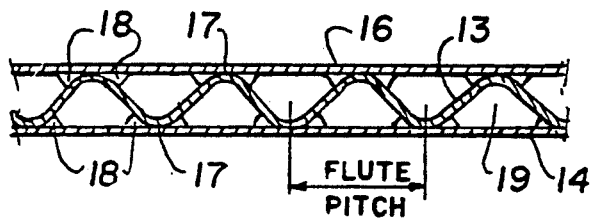
FIG. 8 is a cross sectional view of corrugated cardboard produced in connection with the present invention.

More particularly as shown in FIG. 1, there is provided an apparatus and system 11 which is utilized for producing sheets 12 of corrugated cardboard in which a corrugated sheet 13 is disposed between upper and lower sheets or liners 14 and 16 (see FIG. 8). The corrugated sheet 13 is provided with a form which is similar to a sine wave and is provided with peaks 17 which engage the inner surfaces of the liners 14 and 16 and adhered thereto by glue 18 to form glue joints between the peaks and the liners. The valleys between the peaks 17 are identified as flutes 19 with the flute pitch being approximately equal to the spacing of the corrugations.

The apparatus 11 consists of first, second and third rolls which can be characterized as a bottom roll 21, a middle roll 22 and a top roll 23 which carry rolls of the paper to be utilized to make the corrugated cardboard 12. The sheet 26 applied from the bottom roll 21 passes through a glue applicator 27 which is provided with a roller 28 that travels through a heated glue pan 29 and picks up glue therefrom and transfers it to another roller 31 which applies glue to peaks 17 of the corrugated sheet 13. This sheet 13 formed from a sheet 32 passing from the middle roller 22 and passing over an idler 33 and between a pair of corrugated rollers 34 and 36. The corrugated sheet 13 with the grooves thereon is brought into contact with the upper surface of the sheet 26 and is glued thereto so that the sheet 26 forms the outer or bottom liner 14. The corrugated sheet 13 and the outer liner 14 then travel through a second glue applicator 37. The glue applicator 37 is similar to the glue applicator 27 and is comprised of a roller 38 which travels in a heated glue pan 39 to pick up glue and to transfer the same to another roller 41 which transfers glue to the peaks 17 of the other side of the corrugated sheet 13. As soon as the corrugated sheet 13 passes from the glue applicator 37, it is brought into contact with another sheet 46 which is payed off from the top reel 23 and passes over idler roller 47 and under another idler 48 which brings the sheet into contact with the upper glued peaks 17 of the corrugated sheet 13 to provide the top line 16. The portion of the apparatus 11 heretofore described is substantially conventional.

In accordance with the present invention, a sensor 51 is provided which is adapted to engage the top liner 16 of the corrugated cardboard 14. The sensor 51 is connected to sensor instrumentation 52. The output of the sensor instrumentation 52 is coupled to a control console 53 of a conventional type which utilizes information being sensed by the sensor 51 for controlling the glue pickup roll 38 to control the amount of glue which is picked up and transferred to the roller 41 and turn to the peaks of the corrugated sheet 13.

Figure 2:
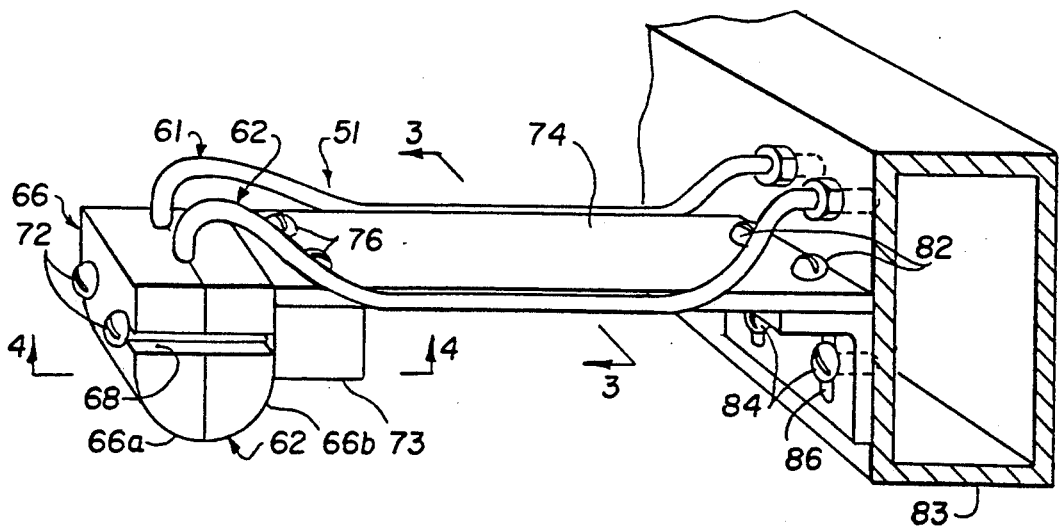
FIG. 2 is a side elevational view of a sensor utilized in the apparatus shown in FIG. 1.

The sensor or sensor apparatus 51 in FIG. 1 is shown in more detail in FIG. 2 and as shown therein is comprised of first and second coaxial lines or tubes 61 and 62 which are capable of carrying high frequency and/or microwave energy. The coaxial lines 61 and 62 have distal extremities 63 and 64 which are carried by a contact or probe head 66. The coaxial lines 61 and 62 run generally parallel to each other and are brought into close contact to each other with their distal extremities being cut off abruptly at the lower extremity of the contact head 66.

Figure 3:
FIG. 3 is a cross sectional view taken along the line 3—3 of FIG. 2.

The contact head assembly 66 is comprised of two usually molded parts 66a and 66b with outwardly open slots 67 and 68 provided on opposite sides of the same which are adapted to be brought into registration with each other. Each part is also provided with semi-circular slots 69, and 71 extending vertically of the parts and opening outwardly through the innermating surfaces of the parts 66a and 66b to provide vertical channels for the coaxial lines 61 and 62. The two parts 66a and 66b are fastened together in a suitable manner such as by a pair of screws 72 extending through the slots 67 and 68 and threaded into support block 73. The support block 73 is carried by the distal extremity of a spring arm or plate 74 formed of a suitable spring material as for example spring steel or phosphor bronze. As hereinafter described the spring arm 74 is positioned to apply a light yieldable force to maintain the contact assembly 66 in engagement with the surface of the material on which measurements are to be made, as for example the presence or absence of glue lines in corrugated cardboard 12. The distal extremity of the spring arm 74 is secured to the support block 73 by a suitable manner such as by screws 76. By way of example, the spring arm 74 could have a length ranging form 6-8" and a width ranging from 1" and a suitable thickness as for example 0.02'. In order to minimize the movement between the spring arm 74 and the coaxial lines 61 and 62, the coaxial lines are bonded to the sides of the spring arm 74 as shown in particular in FIG. 3 in a suitable manner such as by an adhesive.

The parts 66a and 66b of the contact head assembly 66 are formed of an abrasion resistant material which also is thermally and electrically conductive. One material found particularly suitable for these parts 66a and 66b is Lanxide (trademark) manufactured by Lanxide Electronics Components, LP., located at 1300 Marrows Road, Newark, Del., 19714-6077. The material is identified as MCX622 and is comprised of an aluminum saturated matrix of silicon carbide crystals. The aluminum in the Lanxide material provides structural strength while at the same time providing high thermal conductivity and good electrical conductivity. The silicon carbide content of the material provides outstanding abrasion resistance so that in combination the material provides a thermal conductivity and an electrical conductivity almost as good as pure aluminum and abrasion resistance almost as good as that of silicon carbide. The data supplied on the Lanxide material shows that it has an abrasion test volume loss substantially less than that of stainless steel. This is a very desirable characteristic for the contact head assembly 66 so that it will have a long life in industrial application making possible infrequent changing of the contact head assembly 66. Since the material for the parts 66a and 66b is very hard, it must be molded into the desired shape as for example the shapes described above. The Lanxide material used for the parts 66a and 66b also has an additional advantage in that it is very light as for example a specific gravity similar to that of aluminum. This is desirable to provide a low mass at the distal extremity of the spring arm or plate 74 to thereby make it possible for the contact head assembly 66 to be maintained in intimate contact with the body of material being probed and permitting a rapid relative movement between the contact head assembly 66 and the body of material without skipping or jumping when undulations occur in the body material.

The lower surfaces of the parts 66a and 66b are arcuate and rounded so that when the two parts 66a and 66b are mated, semi-cylindrical surfaces, as for example ⅛" in radius, are provided so that the head assembly 66 makes contact with the surface to be contacted along an imaginary line which extends through the two extremities of the coaxial lines 61 and 62. A suitable yieldable force applying the contact head assembly to the material being probed was found to range from 5 to 20 grams and preferably approximately 10 grams.

In considering possible substitutes for the Lanxide material, materials having a thermal conductivity degraded by a factor of two over that provided by aluminum and having an electrical conductivity degraded by a factor of 5 with respect to aluminum could be utilized. With respect to abrasion resistance, degradation of abrasion resistance can be tolerated depending upon the application and the degree to which replacement of the contact heads is economically feasible.

Figure 4:
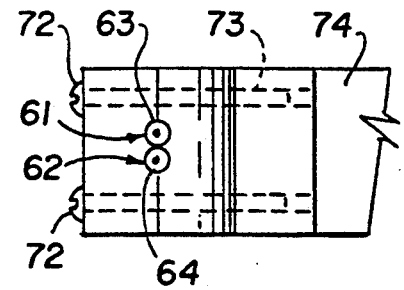
FIG. 4 is a bottom plan view taken along the line 4—4 of FIG. 2.

The proximal extremity of the spring arm 74 is secured to a right angle bracket 81 by suitable means such as screws 82. The bracket 81 is secured to a mounting bar 83 by suitable means such as screws 84 extending through vertically extending slots 86 provided in the bracket 81 permitting the bracket 81 to be adjusted vertically of the bar 83. This makes it possible to adjust the spring force which is applied by the spring arm 74 to the contact head assembly 66 to maintain it in light engagement with the surface of the material to be contacted and on which measurements are to be made. As shown particularly in FIG. 4, the distal extremities of the two coaxial lines 61 and 62 are flush with the semicircular contact surface of the contact head assembly 66.

As is well known to those skilled in the art, the spring arm is designed keeping in mind the dynamic calculations which of necessity must consider the mass of the head assembly 66, the moment inertia of the coaxial lines 61 and 62, the moment of inertia of the spring arms 74. Also to be considered should be the vibration which is introduced into the contact head 66 during relative movement between the head 66 and the material which is being probed to ensure that a negative G acceleration is not encountered. In other words, it is desirable that the spring arm 74 provide approximately constant load to the contact head assembly 66 over a relatively large deflection distance for the head assembly.

Figure 5:
FIG. 5 is a cross sectional view of the coaxial transmission line shown in FIG. 2.

A cross sectional view of the coaxial line 61 is shown in FIG. 5. The other coaxial line 62 is substantially identical. By way of example, the coaxial lines 61 and 62 can have a characteristic 50 ohm impedance. They are provided with a center copper conductor 91 with a suitable diameter as for example 0.025' which is surrounded by a solid cylindrical spacer 92 of a suitable insulating or dielectric material such a Teflon (trademark) and of a suitable outside diameter as for example 0.085'. The dielectric spacer 92 is covered by a jacket 93 serving as an outer shield and formed of a suitable conducting material such a copper which typically can be either tin plated or silver plated.

In accordance with the present invention, it is desirable that the coaxial lines 61 and 62 operate in a frequency range from approximately 10 megahertz to 20 gigahertz and in the present invention at a frequency of 915 megahertz which is the center of the United States spectral band for industrial, scientific and medical uses.

Although the present invention has been described in conjunction with coaxial lines, it should be appreciated that if higher frequencies are desired that circular, ridge, elliptical or rectangular waveguides can be utilized for very shallow penetrations. This would permit operation up to as high as 140 gigahertz. Lower frequencies are utilized when it is desired to penetrate thicker materials. In chosing a frequency, it is also desirable to ascertain the type of resolution desired in the measurements being made.

Figure 6:
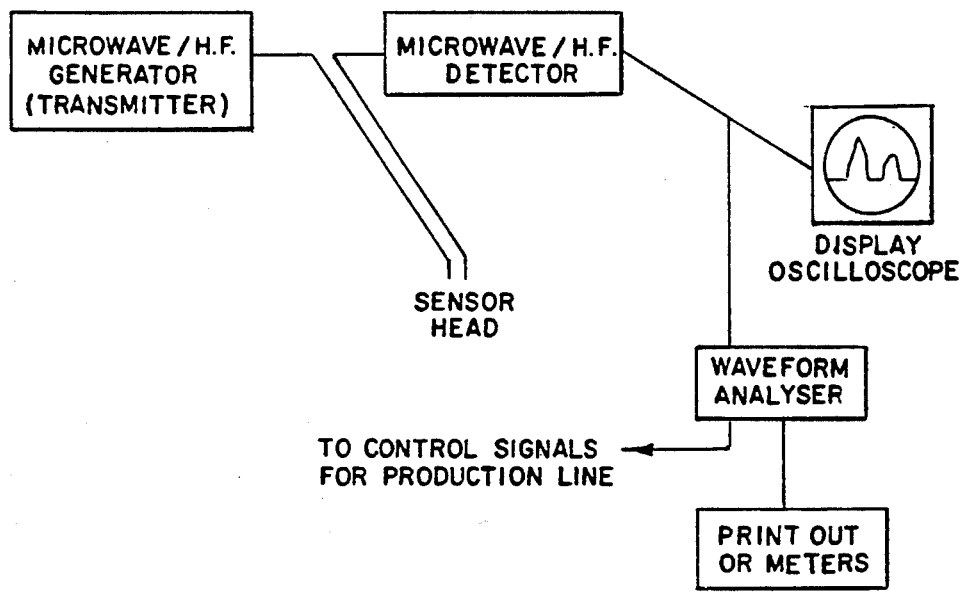
FIG. 6 is a block diagram of the electronic instrumentation used with the sensor shown in FIG. 2 and which is utilized in the apparatus and system shown in FIG. 1.

The sensor instrumentation 52 is shown in more detail in FIG. 6. As shown therein it consists of a high frequency microwave generator 101 of a conventional type to generate power range from 0.1 of a milliwatt to approximately one watt in the desired frequency. By way of example in connection with the apparatus shown in FIG. 1, a frequency of 915 megahertz was selected with a power output of 10 milliwatts. This electrical energy was supplied to the coaxial line 61 to produce at the distal extremity 63 a highly localized high frequency electromagnetic field as hereinafter described that passes into the body of material engaged by the contact head 66 which as shown can be in the form of corrugated cardboard 12. Any of the electric field created at the distal extremity 63 and coupled to and sensed by the distal extremity 64 of the coaxial line 62 is supplied to a high frequency or microwave detector 102 which provides an analog or digital output 103 that is supplied to a display oscilloscope 104 to generate a waveform 106 depicting the sensed information. The same output 103 can be supplied through a line 107 to a waveform analyzer 108 which is provided with an output 109 supplied to a suitable printout device or meters 111 as for example a plotter. The waveform analyzer 108 is also provided with an output 112 that supplies control signals to the control console 53 to control the apparatus in the production line for the corrugated cardboard 12.

Figure 7A:
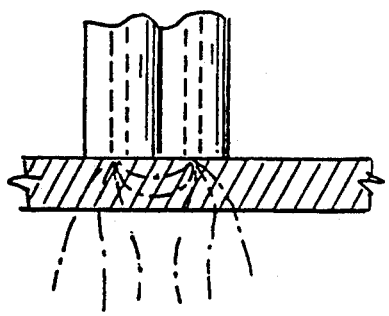
FIG. 7A is a schematic illustration showing the highly localized high frequency electric field which is generated at the distal extremities of the contact head shown in FIG. 2 when in close proximity to or in contact with a poorly conducting body of material and the low level of coupling between the transmitting and receiving coaxial lines.

The operation and use of the apparatus and system 11 utilizing microwave or high frequency energy for making moisture measurements in accordance with the method of the present invention may now be briefly described as follows. Let it be assumed that it is desired to ascertain the amount of glue which is being applied to the peaks 17 of the corrugated sheet 13 which is to be utilized to form joints between the peaks 17 and the inside surface of the top liner 16. The sensor instrumentation 52 supplies high frequency or microwave energy through the coaxial line 61 which creates a highly localized high frequency electromagnetic field represented by the electric field lines 116 in FIG. 7A which pass through the top liner 16, a poorly conducting medium.

The electric field is in effect a leakage or fringe radiation field from the distal extremity of the transmission coaxial line 61. A very small amount of this electric field is coupled into the nearby similarly interrupted receiving coaxial line 62 as represented by the electric field line 117 in FIG. 7A. In connection with the present invention, it has been found that this highly localized field created at the distal extremity of the coaxial transmission line 61 is extremely sensitive to any dielectric material which is placed within its zone of major influence which is formed at the two terminated coaxial lines 61 and 62 to thereby provide a transducer for making dielectric measurements.

Figure 7B:
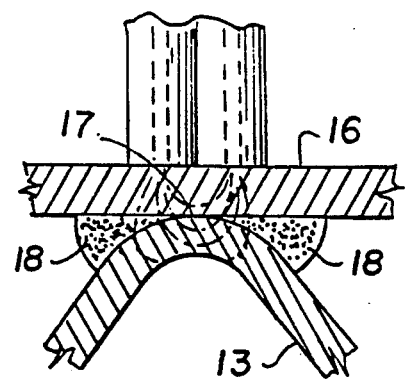
FIG. 7B is a schematic illustration similar to FIG. 7A but showing the manner in which enhanced coupling is provided between the transmitting and receiving coaxial lines when a high dielectric constant body of material is present at the contact head as for example a water containing compound.
Figure 9:
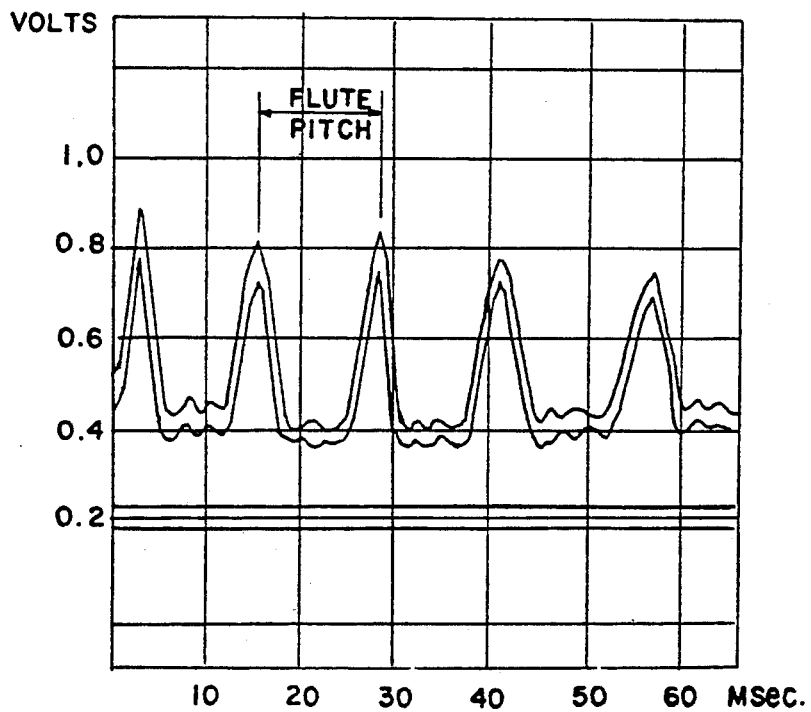
FIG. 9 is a graph showing the manner in which the apparatus and system shown in FIG. 1 can be utilized to ascertain the glue distribution between the corrugations and the top liner of the corrugated cardboard in accordance with the present invention.

As shown in FIG. 7B, when such a transducer comprised of the coaxial lines 61 and 62 probe a body of material having a high dielectric constant and disposed in the zone of major influence of the leakage radiation field, there is provided a greatly enhanced coupling between the transmitting and receiving coaxial lines 61 and 62 represented by the plurality of electric field lines 117. This greatly enhanced coupling is immediately recognized by the detector 102 which supplies a waveform 106 such as shown in FIG. 9 which has peaks 123 that correspond to lines of glue on the peaks 17 of the corrugated sheet 13 as the corrugated cardboard 12 is advanced past the probe or contact head assembly 66 during production in the apparatus shown in FIG. 1. Thus it can be seen that the contact head assembly 66 is in effect measuring the disturbance of the highly localized high frequency field by the corrugated cardboard 12 as it passes underneath the contact head 66. This ability to sense the glue lines 18 is made possible because the highly localized high frequency fields are distorted preferentially and very strongly by any moisture that is present. Since the glue utilized contains moisture, there is a very large modification of the field as glue the passes under the contact head 66. By measuring the amplitude of the field detected, it is possible to obtain a very accurate estimate of the amount of water in the glue 18 at the joint. Since in the process of manufacturing the corrugated cardboard 12, the ratio of water in the glue is very tightly controlled, measuring the amount of water in the glue in contact with the top liner 16 at the peaks 17, it is possible to directly ascertain the amount of glue that is in contact with this top liner 16 and carried by the peaks 17.

This measuring technique is particularly efficacious for use in the manufacture of double sided corrugated cardboard. In the process of manufacturing the corrugated cardboard it is possible to obtain good adhesion between the peaks 17 on the bottom side of the corrugated sheet 13 because the toothed roller 36 applies pressure to the joints between the corrugated sheet 13 and the bottom liner 14. When the top liner 16 is being placed, access cannot be had to the corrugated sheet 13 so that the present invention is very desirable for measuring the amount of glue on the peaks 17 which adhere to the upper liner 16.

By way of example in connection with the present invention, the receiving coaxial line 62 would see approximately 1/1000 of a microwatt of electrical energy when measuring the moisture content of very dry paper with no glue present on the far side. On the other hand, with a heavy glue line present on the far side, an output of 0.1 milliwatt could be achieved from the receiving coaxial line 62. In the graph shown in FIG. 9, the detector base line 121 appears at 0.2 of a volt whereas the bottom portions 122 at approximately 0.4 volts of the waveform 106 the top liner 16 and represents a measurement that is a combination of thickness and moisture content of the liner. The peaks 123 which appear at approximately 0.8 volts have heights which represents the glue line response and the variation in the glue lines which are encountered in the corrugated cardboard at it passes under the contact head or probe 66.

In connection with the present invention, the contact head 66 was provided with two very closely spaced coaxial lines 61 and 62 which have zones of sensitivity which can be generally represented as semi-circles with the diameters of the semi-circles passing through the centers of the distal extremities 63 and 64 of the coaxial lines 61 and 62. With the coaxial lines having a diameter of suitable diameter as for example 0.085", the center to center spacing between the two coaxial lines would be approximately 0.085". Thus, the zone of sensitivity is also a hemisphere of approximately 0.085" in diameter. The electromagnetic field created at the distal extremity 63 of the coaxial line 61 is primarily dominated by its electrostatic characteristics. The coupling between the distal extremities 63 and 64 of the coaxial lines 61 and 62 in the absence of any added material is very weak. Typically power losses can be 1,000,000:1 up to 1,000,000,000:1. As explained previously, the addition of any material in this field enhances the coupling between the transmitting and receiving probes in the form of the distal extremity 63 and 64 of the coaxial lines 61 and 62. The amount of enhancement is a function of the dielectric mass of a body of material that is in the vicinity of the distal extremities of the coaxial lines 61 and 62 in which the distal extremities can be considered to be transmitting and receiving probes. As explained above, the amount of enhancement is a function of the content of any high dielectric constant components in the material. As for example, water has a very high dielectric constant on the order of 70 times that of ambient air. Paper may have a dielectric constant in the amount of 2–6 times that of ambient air. Thus the apparatus and system hereinbefore described will have moderate sensitivity to the presence of a dielectric such as paper and will be extremely sensitive to the presence of any moisture in the vicinity of the coaxial electric fields which couple the probes to each other. Although the probes or distal extremities 63 and 64 of the lines 61 and 62 have been described as being in relatively close proximity to each other, it should be appreciated that some spacing between the coaxial lines can be permitted when that is necessary. However, it is believed that the maximum spacing that should be permitted between the distal extremities of the coaxial lines 61 and 62 should not exceed 2–3 times the diameter of one of the coaxial tubes.

In selecting the diameter of the coaxial lines, it is desirable to select the diameter so that the spacing between the centers of the coaxial lines is less than the minimum resolution desired from the contact head assembly. Thus, by was of example, if the flute pitch in the corrugated cardboard 12 shown in FIG. 8 is 0.3", then the spacing between the centers of the two coaxial lines 61 and 62 should be less than this amount and preferably approximately one fourth of the flute pitch. In the case of the present invention a spacing of 0.085" is provided which readily satisfies this requirement.

Although the present invention has been principally described in connection with the sensing of moisture in corrugated cardboard to ascertain whether there is adequate glue provided in the joints between the upper peaks of the corrugated sheet and the upper liner, there are other numerous applications of the present invention. For example, such moisture sensing apparatus can be utilized for measuring the general moisture content of paper as it comes into a plant or as it is being fed through a paper mill. This can be accomplished by providing a hand held instrument incorporating the apparatus of the present invention which can be utilized for incoming quality inspection.

In another application, the sensor apparatus of the present invention can be utilized for drying sheet materials by controlling the application of heat to the material to remove excess moisture as for example from paper in which the sensor apparatus of the present invention can be utilized to control the time that the paper is exposed to the heat to thereby control the removal of moisture from the sheets of paper.

Other applications in which the invention can be utilized are measuring the thickness of paint after it has been applied either to a metallic background or to a background that has a dielectric constant significantly different from that of paint. Such an apparatus and method is particularly useful because it is non destructive of the painted surface.

Another application is measuring the thickness of egg shells after they have been layed which information can be utilized to control the balance of the diet that is fed to the egg laying hens. Also the thicknesses of wax surfaces on leaves of trees can be measured to ascertain the health of the trees which for example can be correlated with the projected productivity of citrus from the trees. Medical applications include the ability to differentiate between fatty tissue and non-fatty tissue close to human skin.

In view of the foregoing, it can be seen that the moisture measurement apparatus, system and method utilizing microwave or high frequency energy has many applications making it possible to measure non destructively the thicknesses of various bodies of materials having substantially different dielectric constants. Since water has a high dielectric constant, some materials having water therein also have a high dielectric constant making such materials particularly suitable for measurement in accordance with the present invention.

I claim:

1. In apparatus for sensing the amount of glue being applied to the peaks of a corrugated sheet to be disposed between upper and lower sheets to form cardboard having first and second substantially parallel surfaces, a sensor device comprising first and second substantially parallel coaxial lines having distal extremities in relatively close proximity to each other and adapted to be disposed in close proximity to the cardboard solely on one side of the cardboard adjacent said first surface, transmitter means coupled to the first coaxial line for introducing electrical energy in the high frequency to a microwave range into the first coaxial line to cause a fringe radiation field to be established at the distal extremity of the first coaxial line and to extend into the cardboard, receiving means coupled to the second coaxial line for detecting any of the fringe radiation field coupled into it from the first coaxial line and measurement means coupled to the receiving means for ascertaining when any change occurs in the coupling of the fringe radiation field from the first coaxial line to the second coaxial line.

2. Apparatus as in claim 1 wherein the sensor device includes a contact head adapted to be positioned in close proximity to said first surface and wherein the distal extremities of the coaxial lines are mounted in said contact head.

3. Apparatus as in claim 2 wherein said contact head has an arcuate surface and wherein the distal extremities of the first and second coaxial lines extend through said arcuate surface.

4. Apparatus as in claim 2 wherein said contact head is formed of an abrasion resistant material having high thermal and electrical conductivity.

5. Apparatus as in claim 4 wherein said contact head is formed of material which has a thermal conductivity and electrical conductivity which approximates that of aluminum.

6. Apparatus as in claim 5 wherein said contact head is formed of a silicon carbide impregnated with aluminum.

7. Apparatus as in claim 2 wherein said head is formed of Lanxide.

8. Apparatus as in claim 2 together with spring means secured to said contact head for yieldably urging said contact head into engagement with said body of material with a relatively light force.

9. Apparatus as in claim 8 wherein said spring means is in the form of a spring arm secured to said contact head and means for adjusting the position of the contact head to vary the pressure with which the contact head is yieldably urged into engagement with the body of material.

10. Apparatus as in claim 8 wherein said relatively light force is in the order of 5 to 20 grams.

11. In a system for measuring the moisture content of corrugated cardboard, first, second and third rolls of sheets of paper, means for advancing the sheet of paper from the first roll so that it serves as a bottom liner for the corrugated cardboard, means for withdrawing the sheet of paper from the second roll and forming corrugations in the sheet of paper so that the sheet of paper has peaks disposed on opposite sides thereof, means for applying glue to the peaks of the bottom side of the sheet of paper and causing the peaks to come into contact with the sheet of paper from the first roll so that the corrugated sheet is adhered to the bottom liner, means for applying the glue to the peaks on the opposite side of the corrugated sheet and means for withdrawing paper from the third roll of paper and bringing it into engagement with the peaks on the opposite side having glue thereon to form a top liner, a contact head engaging the top liner on the side opposite engaging the peaks of the corrugated sheet, said contact head having first and second coaxial lines extending therethrough in a substantially parallel directions in close proximity to each other and engaging the top surface of the top liner, means for introducing high frequency or microwave energy into the first coaxial line to cause a fringe radiation field to be created at the distal extremity of the first coaxial line and extending through the top liner, detector means coupled to the second coaxial line for detecting any of the fringe radiation field produced by the first coaxial line which is coupled into the distal extremity of the second coaxial line and measurement means coupled to the detector means for ascertaining when enhancement of the coupling of the fringe radiation field between the distal extremities of the first and second coaxial lines occurs to thereby ascertain the presence of moisture in the glue securing the top liner to the corrugated sheet and means responsive to the sensed information for controlling the application to the glue of the peaks in the upper side of the corrugated sheet.

12. A system as in claim 11 wherein the corrugated cardboard is moved relative to the contact head.

13. A system as in claim 12 wherein the corrugated cardboard is moved in a direction which is perpendicular to the direction of the corrugations in the corrugated cardboard.

14. A system as in claim 11 together with means secured to the contact head for yieldably urging the contact head into engagement with the upper surface of the top liner.

15. A system as in claim 11 wherein the contact head is formed of an abrasion resistive material having high thermal and electrical conductivity.

* * * * *